United States Patent [19]

Hull

[11] Patent Number: 5,190,056

[45] Date of Patent: Mar. 2, 1993

[54] PORTABLE DEVICE FOR SUPPORTING AN INJURED PERSON

[76] Inventor: Michael C. Hull, 4142 Crossing La., Dallas, Tex. 75220

[21] Appl. No.: 834,488

[22] Filed: Feb. 12, 1992

[51] Int. Cl.[5] .............................................. A61F 5/37
[52] U.S. Cl. ......................................... 128/870; 3/621
[58] Field of Search .................... 5/601, 625; 128/870, 128/871; 378/180, 208, 209

[56] References Cited

U.S. PATENT DOCUMENTS

| 2,508,449 | 5/1950 | Davis | 5/601 |
|---|---|---|---|
| 3,215,834 | 11/1965 | Tayman | 5/601 |
| 3,648,305 | 3/1972 | Ersek | 5/601 |
| 3,737,923 | 6/1973 | Prolo | 128/870 |
| 3,840,221 | 10/1974 | Hogan | 5/601 |
| 3,889,668 | 6/1975 | Och et al. | 128/870 |
| 4,034,748 | 7/1977 | Winner | 128/870 |
| 4,067,565 | 1/1978 | Daniels | 5/601 |
| 4,127,120 | 11/1978 | Applegate | 128/870 |
| 4,226,231 | 10/1980 | Andersen | 128/870 |
| 4,369,982 | 1/1983 | Hein | 128/870 |
| 4,506,664 | 3/1985 | Brault | 128/870 |
| 4,665,574 | 5/1987 | Filips | 5/601 |
| 4,667,355 | 5/1987 | Nishijima | 5/625 |
| 4,854,305 | 8/1989 | Bremer | 128/870 |
| 4,895,173 | 1/1990 | Brault et al. | 128/870 |
| 5,088,137 | 2/1992 | Rose | 128/870 |

Primary Examiner—Robert A. Hafer
Assistant Examiner—Michael Brown
Attorney, Agent, or Firm—W. Kirk McCord

[57] ABSTRACT

A device for supporting and transporting an injured person includes a generally rectangular board for supporting the person in a supine position. The board is formed of a radiolucent material and has relatively flat opposed top and bottom surfaces, opposed first and second sides and opposed first and second ends. The board has a plurality of slots spaced longitudinally along the board between the top and bottom surfaces. Each of the slots is adapted to receive a radio-imaging plate with the plate oriented substantially parallel to the top and bottom surfaces for anterior/posterior radio-imaging of the person's body. First and second laterally spaced projections extend upwardly from the top surface adjacent the first side and third and fourth laterally spaced projections extend upwardly from the top surface adjacent the second side. The first and second projections define a first groove therebetween and the third and fourth projections define a second groove therebetween. The first and second grooves are adapted to receive a radio-imaging plate with the plate oriented substantially perpendicular to the top and bottom surfaces for lateral radio-imaging of the person's body. Respective portions of the first and fourth projections extend outwardly from the respective first and second sides to define respective elongated first and second handles.

20 Claims, 2 Drawing Sheets

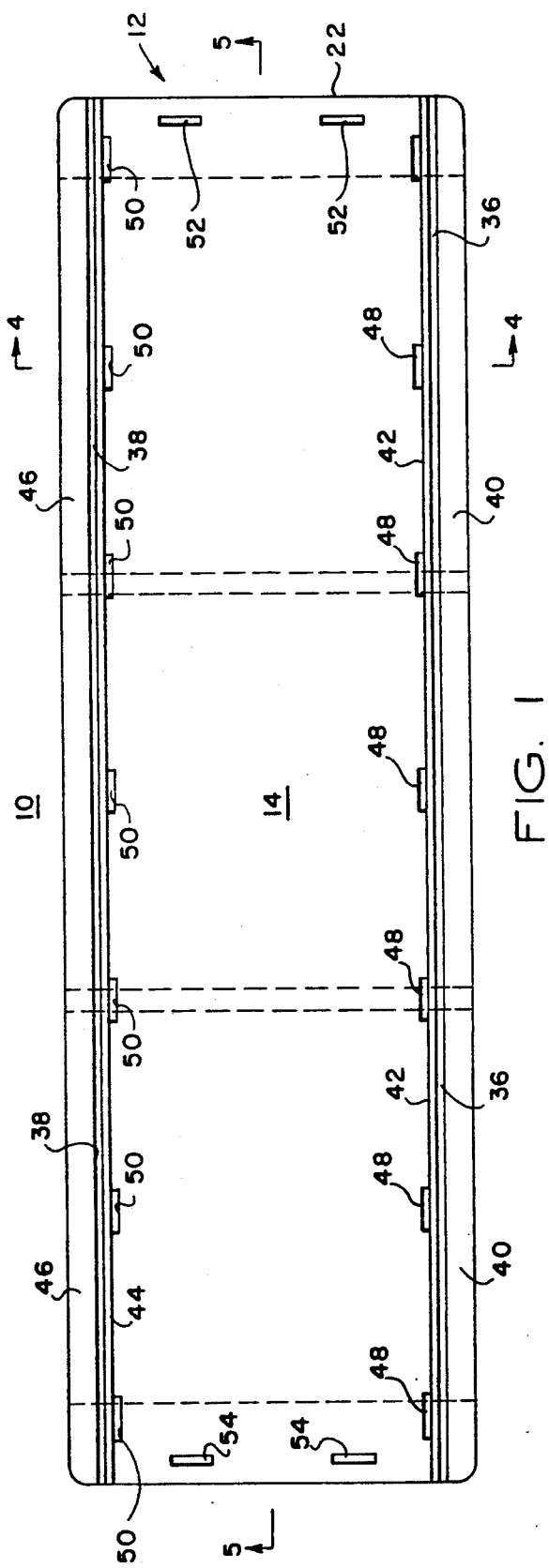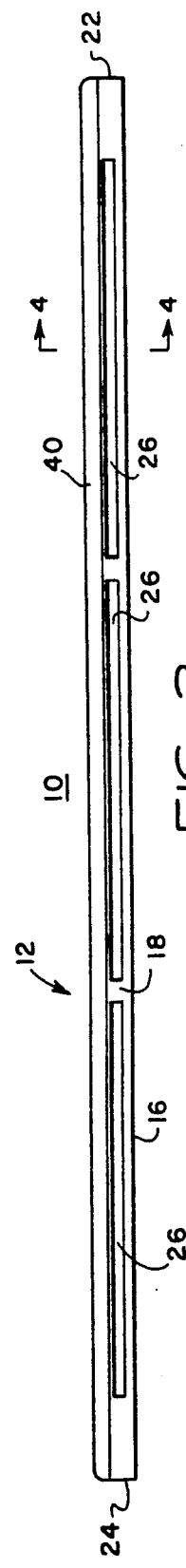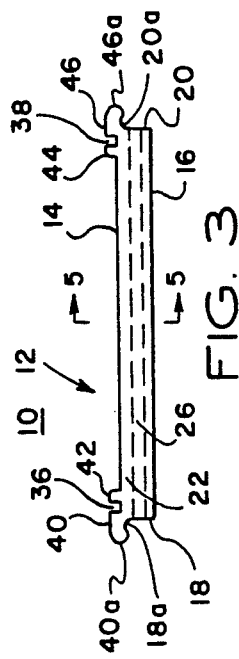

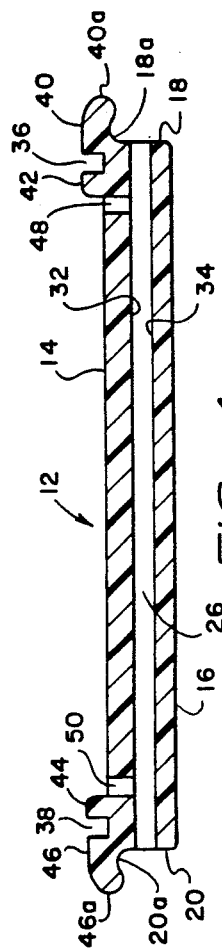
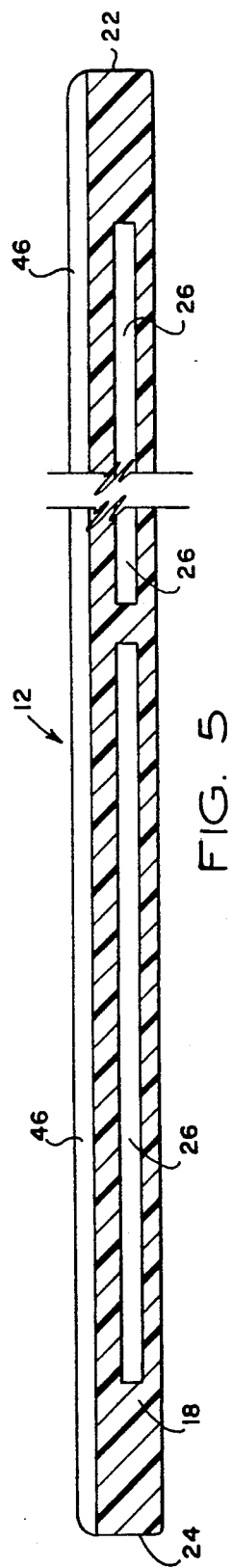
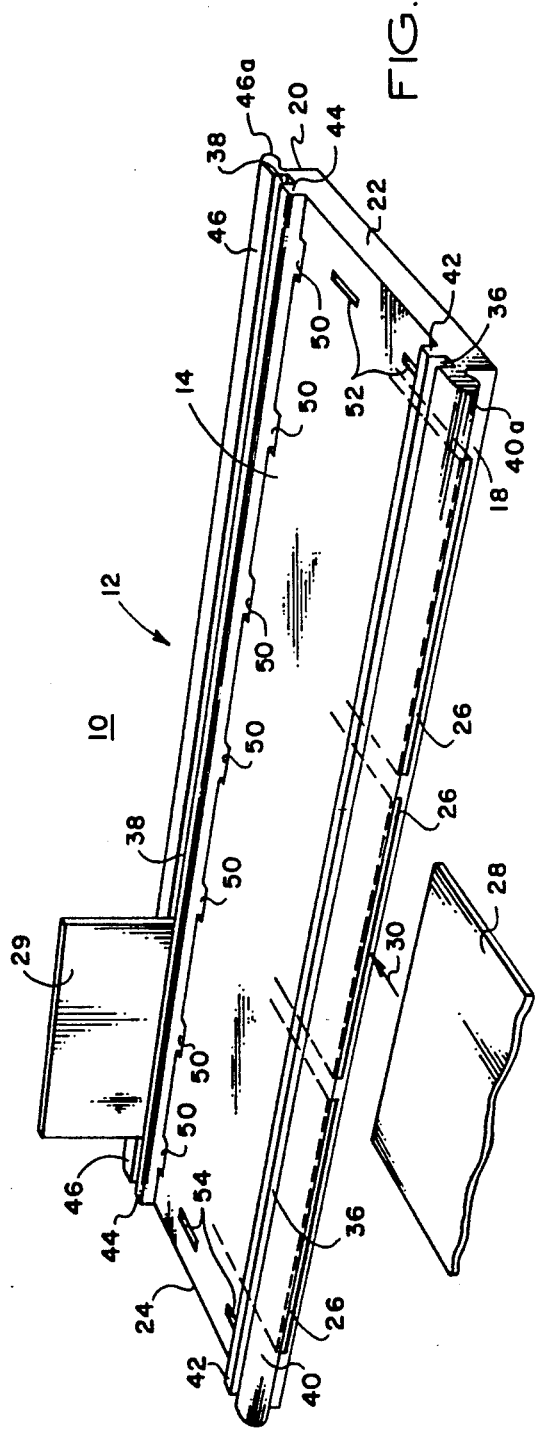

PORTABLE DEVICE FOR SUPPORTING AN INJURED PERSON

FIELD OF INVENTION

This invention relates generally to medical devices and in particular to a portable device for supporting an injured person which is compatible for use with radiolucent machines, such as X-ray machines.

BACKGROUND OF THE INVENTION

Those familiar with rescue and emergency equipment for use with injured persons will readily appreciate that it is often-times critical to completely immobilize an injured person at the scene of the accident, to avoid exacerbating individual's injury and occasioning further trauma. This is particularly true with respect to cervical or spinal injuries where movement of the individual immediately subsequent to the injury may result in further, and potentially permanent, damage, for example, to the nerves governing motor movement. Equally critical, however, is the need to maintain the patient immobilized until diagnostic tests can be performed and a course of action determined.

DESCRIPTION OF THE PRIOR ART

It is known in the art to provide a rigid board for supporting an injured person in a supine position. Adjustable straps are typically provided for immobilizing the patient on the board. Examples of prior art transport devices are disclosed in U.S. Pat. Nos. 3,737,923; 3,889,668; 4,034,748; 4,127,120; 4,226,231; 4,854,305; and 4,895,173.

Medical treatment of an injured person may involve certain diagnostic tests, including the use of radio-imaging equipment and procedures, such as computer-aided tomography (C.T.), X-ray, and magnetic resonance imaging (M.R.I.). Many prior art portable devices for supporting an injured person are formed of metal parts which are not compatible with such radio-imaging equipment and procedures. One solution, of course, is to remove the patient from the device and dispose the patient on another support compatible for use with the particular diagnostic equipment and procedure. However, this is wholly contrary to the need to maintain the patient immobilized until a proper course of treatment can be determined. It is therefore highly desirable to maintain the patient in an immobilized condition as soon after the injury as possible and to maintain the patient immobilized both during transport and while the diagnostic procedures are being performed.

U.S. Pat. No. 4,854,305 discloses a radiolucent transport and diagnostic procedure board, which is formed of an expanded foam plastic core covered with an acrylic resin lamination, so that the board is compatible for use with radio-imaging equipment. However, in order to perform radio-imaging procedures, such as X-ray imaging, the board must be positioned with respect to an X-ray imaging machine to allow the necessary diagnostic procedures to be performed. As such, the board may have to be repositioned several times with respect to the X-ray equipment in order to achieve the desired X-ray views. There is therefore a need for an improved portable device for supporting an injured person which is compatible with radio-imaging equipment and procedures, such as X-ray imaging.

DISCLOSURE OF THE INVENTION

In accordance with the present invention, a portable device is provided for supporting an injured person. The device includes a radiolucent board for supporting the person in a supine position. The board has relatively flat, opposed top and bottom surfaces.

In accordance with a feature of the invention, the board includes a slot intermediate the top and bottom surfaces and adapted to receive a radio-imaging plate with the plate oriented substantially parallel to the top and bottom surfaces for anterior/posterior radio-imaging of the person's body. The board further includes a groove adjacent the top surface of the board and adapted to receive a radio-imaging plate with the plate oriented substantially perpendicular to the top and bottom surfaces for lateral radio-imaging of the person's body.

In accordance with another feature of the invention, the device includes a plurality of handles projecting from the board, to facilitate lifting and carrying the board with the injured person supported thereon. In accordance with yet another feature of the invention, the device further includes means for substantially immobilizing the injured person on the board.

In the preferred embodiment, the board is generally rectangular with opposed first and second sides and opposed first and second ends. The board has a plurality of side openings communicating between the top and bottom surfaces adjacent each of the first and second sides and a plurality of end openings communicating between the top and bottom surfaces adjacent each of the first and second ends. Each of the side openings adjacent the first side is adapted to cooperate with a side opening adjacent the second side for receiving a lateral securing member. Similarly, each of the end openings adjacent the first end is adapted to cooperate with an end opening adjacent the second end for receiving a longitudinal securing member. The lateral and longitudinal securing members are operable for securing the person in an immobilized position on the board.

In the preferred embodiment, the device further includes first and second laterally spaced projections extending upwardly from the top surface of the board adjacent the first side thereof and third and fourth laterally spaced projections extending upwardly from the top surface of the board adjacent the second side thereof. The first and second projections define a first groove therebetween for receiving a radio-imaging plate adjacent the first side of the board, with the plate oriented substantially perpendicular to the top and bottom surfaces. The third and fourth projections define a second groove therebetween for receiving a radio-imaging plate adjacent the second side of the board, with the plate oriented substantially perpendicular to the top and bottom surfaces. Respective portions of the first and second projections extend outwardly from the respective first and second sides of the board to define respective elongated first and second handles.

The device preferably further includes a plurality of slots intermediate the top and bottom surfaces of the board. Each of the slots communicates between the first and second sides of the board, such that each slot is adapted to receive a radio-imaging plate which is inserted into the corresponding slot along a lateral axis of the board.

The device according to the present invention is compatible with radio-imaging equipment and procedures, such as X-ray imaging. The device is able to accommodate radio-imaging plates so that various views of the person's injuries can be obtained without having to move the injured person.

BRIEF DESCRIPTION OF THE DRAWINGS

FIG. 1 is a top plan view of a portable device for supporting an injured person, according to the present invention;

FIG. 2 is a side view of the device of FIG. 1;

FIG. 3 is an end view of the device of FIG. 1;

FIG. 4 is a sectional view of the device, taken along the line 4—4 of FIG. 2;

FIG. 5 is a sectional view of the device, taken along the line 5—5 of FIG. 1; and FIG. 6 is a perspective view of the device, illustrating the accommodation of one or more radio-imaging plates.

DETAILED DESCRIPTION OF THE PREFERRED EMBODIMENT

In the description which follows, like parts are marked throughout the specification and drawings with the same respective reference numerals. The drawings are not necessarily to scale and in some instances proportions may have been exaggerated in order to more clearly depict certain features of the invention.

Referring to FIGS. 1-3, a portable device 10 for supporting an injured person in a supine position includes a generally rectangular, rigid board 12, which is formed of a light-weight, radiolucent material, such as plastic. Plastic material provides several advantages over the wood material used in many prior art transport boards, including increased tensile strength compared to wood boards of equal thickness and a lighter weight, to facilitate handling and transporting board 12 with an injured person supported thereon. Furthermore, the plastic material will not splinter like wood material, which may injure the hands of the transport personnel, resulting not only in pain, but also potential infection, which is particularly important in view of the current AIDS epidemic. Board 12 includes relatively flat, opposed top and bottom surfaces 14 and 16, respectively, opposed first and second sides 18 and 20, respectively, and opposed first and second ends 22 and 24, respectively.

Referring also to FIGS. 4 and 5, board 12 has three slots 26 intermediate top and bottom surfaces 14 and 16. Each slot 26 communicates between first and second sides 18 and 20 and is adapted to receive a radio-imaging plate 28, such as an X-ray "buckie", which is inserted into the corresponding slot 26 along a lateral axis of board 12. FIG. 6 shows a relatively flat radio-imaging plate 28 being inserted into the middle slot 26 of board 12 along a lateral axis of board 12, as indicated by arrow 30.

As can be best seen in FIGS. 4 and 5, the thickness of the solid portion of board 12 between top surface 14 and an upper surface 32 of each slot 26 is approximately ¼ inch. The height of each slot 26, as measured between upper surface 32 and lower surface 34 of the corresponding slot 26, is also approximately ¼ inch. The thickness of the solid portion of board 12 beneath each of the slots 26, as measured from lower surface 34 of each slot 26 to bottom surface 16, is also approximately ¼ inch.

In the preferred embodiment, board 12 has a length of approximately six feet, as measured between first and second ends 22 and 24, and a width of approximately 18 to 22 inches, as measured between first and second sides 18 and 20, to accommodate most adult patients. Board 12 may be downsized to accommodate children. For example, a typical device 10 for transporting injured children may include a plastic board 12 which is approximately four feet long and 16 inches wide. Although not shown in the drawings, a pad made of a soft material, such as foam rubber, is preferably positioned on top surface 14 to enhance patient comfort by preventing direct contact between the patient's body and board 12. The pad is preferably ½ inch to 1½ inches thick and is comprised of a radiolucent material.

As can be best seen in FIGS. 2, 4, 5 and 6, the three slots 26 are spaced longitudinally along board 12 so that various anterior/posterior views of the patient's body can be obtained using radio-imaging equipment, such as an X-ray machine. Device 10 is also compatible for lateral views using radio-imaging equipment. Device 10 includes first and second elongated grooves 36 and 38, respectively, adjacent the respective first and second sides 18 and 20. Grooves 36 and 38 extend substantially the entire length of board 12, between first and second ends 22 and 24. As can be best seen in FIGS. 3, 4 and 6, first and second grooves 36 and 38 are defined by first and second pairs of projections extending upwardly from top surface 14. The first pair of projections includes first and second projections 40 and 42, respectively. The second pair of projections includes third and fourth projections 44 and 46, respectively. First and second projections 40 and 42 are laterally spaced adjacent first side 18 and extend along the entire length of board 12 between first and second ends 22 and 24, to define first groove 36 therebetween. Third and fourth projections 44 and 46 are laterally spaced adjacent second side 20 and extend along the entire length of board 12 between first and second ends 22 and 24, to define second groove 38 therebetween.

Respective portions of first and fourth projections 40 and 46 extend outwardly from respective sides 18 and 20 to define respective peripheral handles extending along substantially the entire length of the respective sides 18 and 20. The respective extension portions have respective bulbous ends 40a and 46a, which are curved slightly downward, as can be best seen in FIGS. 3 and 4. Bulbous ends 40a and 46a define respective curved recesses 18a and 20a on the respective first and second sides 18 and 20. When board 12 is positioned with bottom surface 16 in contact with a relatively flat surface, such as the ground, bulbous ends 40a and 46a are elevated above the ground so that transport personnel can insert their fingers into recesses 18a and 20a beneath the respective bulbous ends 40a and 46a to grasp the handles at any position along the respective sides 18 and 20, thereby facilitating handling and transporting of board 12 with the patient supported thereon.

As can be best seen in FIGS. 1 and 6, board 12 has a plurality of first side openings 48 longitudinally spaced along first side 18 adjacent second projection 42 and a plurality of second side openings 50 longitudinally spaced along second side 20 adjacent third projection 44. A pair of first end openings 52 are located adjacent first end 22 and a pair of second end openings 54 are located adjacent second end 24. First side openings 48, second side openings 50, first end openings 52 and second end openings 54 communicate between top and bottom surfaces 14 and 16. Each of the first side openings 48 is adapted to cooperate with one of the second side openings 50 for receiving a lateral strap (not shown) or other securing member. Similarly, each of the first end openings 52 is adapted to cooperate with one of the second end openings 54 for receiving a longitudinal strap (not shown) or other securing member. The lateral and longitudinal straps are preferably adjustable to maintain the patient in an immobilized position on board 12. The patient is preferably immobilized during both transportation and diagnostic procedures.

As can be best seen in FIG. 6, device 10 is compatible with radio-imaging equipment and procedures, such as X-ray equipment and procedures. Each slot 26 is adapted to receive a relatively flat radio-imaging plate 28 with plate 28 oriented substantially parallel to top and bottom surfaces 14 and 16, to obtain various anterior/posterior views of the patient's body. First and second grooves 36 and 38 are also adapted to receive a radio-imaging plate 29, such as an X-ray buckie, with plate 29 oriented substantially perpendicular to top and bottom surfaces 14 and 16, to obtain various lateral views of the patient's body. First and second grooves 36 and 38 each have a vertical height of approximately ½ to retain plate 29 in a stable upright position. A radio-imaging plate can be positioned at any desired location along the corresponding groove 36 or 38, to obtain the desired lateral view of the patient's body.

One skilled in the art will appreciate that multiple radio-imaging views may be obtained with portable radio-imaging equipment or conventional stationary equipment while maintaining the patient completely immobilized, thereby reducing the likelihood of further injury. By expediting post-injury diagnostic procedures, the location and extent of the patient's injuries can be quickly evaluated and a proper course of action determined. As a result, medical treatment is expedited, which enhances the patient's chances of recovery.

Various embodiments of the invention have now been described in detail. Since it is obvious that many changes in and additions to the above-described preferred embodiment may be made without departing from the nature, spirit and scope of the invention, the invention is not to be limited to said details, except as set forth in the appended claims.

What is claimed is:

1. A portable device for supporting an injured person, said device comprising:
   a radiolucent board having a length sufficient to support the injured person's entire body in a supine position, said board being relatively rigid and having relatively flat, opposed top and bottom surfaces;
   at least one slot intermediate said top and bottom surfaces, said at least one slot being adapted to receive a radio-imaging plate with the plate oriented substantially parallel to said top and bottom surfaces, said at least one slot having sufficient length along said board to permit anterior/posterior radio-imaging of the injured person's entire body without having to move either the person or said board; and
   at least one groove on a top portion of said board, said at least one groove being adapted to receive a radio-imaging plate with the plate oriented substantially perpendicular to said top and bottom surfaces and having sufficient length along said board to permit lateral radio-imaging of the person's entire body without having to move either the person or said board.

2. The device of claim 1 further including means for substantially immobilizing the person supported on the board.

3. The device of claim 2 wherein said means for substantially immobilizing the person includes a plurality of openings communicating between the top and bottom surfaces and adapted to receive a securing member for immobilizing the person.

4. The device of claim 1 wherein said board is generally rectangular with opposed first and second sides and opposed first and second ends.

5. The device of claim 4 wherein said at least one slot communicates between said first and second sides, said at least one slot being adapted to receive a radio-imaging plate which is inserted into said at least one slot along a transverse axis of the board.

6. The device of claim 4 wherein said board has a plurality of first and second side openings communicating between the top and bottom surfaces adjacent the respective first and second sides and a plurality of first and second end openings communicating between the top and bottom surfaces adjacent the respective first and second ends, each of the first side openings being adapted to cooperate with a second side opening for receiving a lateral securing member, each of the first end openings being adapted to cooperate with a second end opening for receiving a longitudinal securing member, said lateral and longitudinal securing members being operable for securing a person in an immobilized position on the board.

7. The device of claim 4 further including first and second handles projecting from the respective first and second sides.

8. The device of claim 7 wherein each of said first and second handles extends between the first and second ends of the board.

9. The device of claim 14 further including first and second laterally spaced projections extending upwardly from the top surface adjacent said first side along substantially the entire length of said board and third and fourth laterally spaced projections extending upwardly from the top surface adjacent the second side along substantially the entire length of said board, said first and second projections defining a first groove therebetween for receiving a radio-imaging plate with the plate oriented substantially perpendicular to the top and bottom surfaces for lateral radio-imaging of the person's entire body, said third and fourth projections defining a second groove therebetween for receiving a radio-imaging plate with the plate oriented substantially perpendicular to the top and bottom surfaces for lateral radio-imaging of the person's entire body.

10. The device of claim 9 wherein respective portions of the first and fourth projections extend outwardly from the respective first and second sides to define respective elongated first and second handles.

11. The device of claim 9 wherein each of said first and second grooves extends substantially the entire length of said board and is adapted to receive a radio-imaging plate to permit lateral radio-imaging of the person's entire body without having to move either the person or said board.

12. The device of claim 10 wherein each of said first and second handles extends substantially the entire length of said board, each of said first and second handles having a curved undersurface to facilitate handling.

13. The device of claim 14 wherein said at least one slot includes a plurality of slots intermediate said top and bottom surfaces at predetermined intervals along substantially the entire length of said board, each of said slots extending transversely between and through said first and second sides and being adapted to receive a radio-imaging plate which is insertable into the corresponding slot along a transverse axis of said board, whereby anterior/posterior radio-imaging of the person's entire body is achievable without having to move either the person or said board.

14. The device of claim 4 wherein said at least one groove includes first and second grooves on top of said board adjacent the respective first and second sides, each of said grooves extending substantially the entire length of said board and being adapted to receive a radio-imaging plate with the plate oriented substantially perpendicular to said top and bottom surfaces to permit lateral radio-imaging of the person's entire body without having to move either the person or said board.

15. The device of claim 1 wherein said at least one slot includes a plurality of slots intermediate said top and bottom surfaces at predetermined intervals along said board, each of said slots being adapted to receive a radio-imaging plate for anterior/posterior imaging of a corresponding portion of the person's body, said slots extending a sufficient length along said board to permit anterior/posterior imaging of the person's entire body without having to move either the person or said board.

16. The device of claim 1 wherein said at least one groove includes first and second grooves adjacent respective opposed sides of said board, each of said first and second grooves extending substantially the entire length of said board for receiving a radio-imaging plate to permit lateral radio-imaging of the injured person's entire body without having to move either the person or said board.

17. A device for transporting said immobilizing an injured person, said device comprising:
   a generally rectangular board having a length sufficient to support the injured person's entire body in a supine position, said board being formed of a radiolucent material and having relatively flat, opposed top and bottom surfaces, opposed first and second sides and opposed first and second ends;
   a plurality of slots spaced longitudinally along substantially the entire length of said board, each of said slots being located intermediate said top and bottom surfaces and being adapted to receive a radio-imaging plate with the plate oriented substantially parallel to said top and bottom surfaces, said slots permitting anterior/posterior radio-imaging of the person's entire body without having to move either the person or said board;
   first and second grooves located adjacent said first and second sides on a top portion of said board, each of said first and second grooves being adapted to receive a radio-imaging plate with the plate oriented substantially perpendicular to said top and bottom surfaces and having sufficient length along said board to permit lateral radio-imaging of the person's entire body without having to move either the person or said board; and
   means for substantially immobilizing the injured person on said board.

18. The device of claim 17 further including first and second laterally spaced projections extending upwardly from the top surface adjacent said first side along substantially the entire length of said board and third and fourth laterally spaced projections extending upwardly from the top surface adjacent said second side along substantially the entire length of said board, said first and second projections defining said first groove therebetween and said third and fourth projections defining said second groove therebetween.

19. The device of claim 18 wherein respective portions of said first and fourth projections extend outwardly from the respective first and second sides to define respective elongated first and second handles.

20. A device for transporting and immobilizing an injured person, said device comprising:
   a generally rectangular board having a length sufficient to support the injured person's entire body in a supine position, said board being formed of radiolucent material and having relatively flat, opposed top and bottom surfaces, opposed first and second sides and opposed first and second ends, said board having a plurality of first and second side openings communicating between said top and bottom surfaces adjacent the respective first and second sides and a plurality of first and second end openings communicating between said top and bottom surfaces adjacent the respective first and second ends, each of said first side openings being adapted to cooperate with a second side opening for receiving a lateral securing member, each of said first end openings being adapted to cooperate with a second end opening for receiving a longitudinal securing member, the lateral and longitudinal securing members being operable to secure the injured person in an immobilized position on said board;
   a plurality of slots spaced longitudinally along substantially the entire length of said board, each of said slots being located intermediate said top and bottom surfaces and being adapted to receive a radio-imaging plate with the plate oriented substantially parallel to said top and bottom surfaces to permit anterior/posterior radio-imaging of the person's entire body without having to move either the person or said board; and
   first and second laterally spaced projections extending upwardly from said top surface adjacent said first side and third and fourth laterally spaced projections extending upwardly from said top surface adjacent said second side, said first and second projections defining a first groove therebetween for receiving a radio-imaging plate with the plate oriented substantially perpendicular to said top and bottom surfaces, said third and fourth projections defining a second groove therebetween for receiving a radio-imaging plate with the plate oriented substantially perpendicular to said top and bottom surfaces, said first and second grooves having sufficient length along said board to permit lateral radio-imaging of the person's entire body without having to move either the person or said board, respective portions of said first and fourth projections extending outwardly from the respective first and second sides to define respective elongated first and second handles, said first and second handles each extending substantially the entire length of said board.

* * * * *